United States Patent
Lee et al.

(10) Patent No.: US 7,341,750 B2
(45) Date of Patent: Mar. 11, 2008

(54) **COMPOUND ISOLATED FROM *GINKGO BILOBA* BARK, ISOLATION METHOD THEREOF AND ANTIPLATELET COMPOSITION CONTAINING THE SAME**

(75) Inventors: Hyun-Jung Lee, Seoul (KR); Hak-Ju Lee, Seoul (KR); Kang-Hoon Je, Seoul (KR); Jeong Kon Seo, Seoul (KR); Seung Jin Lee, Seoul (KR); Sun Li Bang, Incheon (KR)

(73) Assignee: Candleflower Co., Ltd., Icheon (KR)

( * ) Notice: Subject to any disclaimer, the term of this patent is extended or adjusted under 35 U.S.C. 154(b) by 0 days.

(21) Appl. No.: 11/594,545

(22) Filed: Nov. 8, 2006

(65) Prior Publication Data

US 2008/0014293 A1    Jan. 17, 2008

(30) Foreign Application Priority Data

Jul. 14, 2006   (KR) ............. 10-2006-0066084
Jul. 14, 2006   (KR) ............. 10-2006-0066085

(51) Int. Cl.
*A61K 36/16*   (2006.01)

(52) U.S. Cl. .................................... 424/752
(58) Field of Classification Search ............... None
See application file for complete search history.

(56) References Cited

OTHER PUBLICATIONS

Cui et al., Application studies on stereochemistry by NOESY, 1998, Bopuxue Zazhi, vol. 15, pp. 489-494.*

* cited by examiner

*Primary Examiner*—Susan Hoffman
*Assistant Examiner*—Catheryne Chen
(74) *Attorney, Agent, or Firm*—John K. Park; Park Law Firm

(57) ABSTRACT

Disclosed herein are a novel compound isolated from *Ginkgo biloba* and a method for isolating the novel compound from *Ginkgo biloba*. The method comprises: (1) extracting *Ginkgo biloba* with alcohol to obtain a crude extract; (2) subjecting the *Ginkgo biloba* crude extract to solvent fractionation using an organic solvent; (3) fractionating the solvent fractions by Sephadex column chromatography; and (4) fractionating the Sephadex fractions by silica gel column chromatography.

8 Claims, 8 Drawing Sheets

COMPOUND ISOLATED FROM *GINKGO BILOBA* BARK, ISOLATION METHOD THEREOF AND ANTIPLATELET COMPOSITION CONTAINING THE SAME

CLAIMING FOREIGN PRIORITY

The applicant claims and requests a foreign priority, through the Paris Convention for the Protection of Industrial Property, based on patent applications filed in the Republic of Korea (South Korea) with the filing date of Jul. 14, 2006 with the patent application number 10-2006-0066084 and with the filing date of Jul. 14, 2006 with the patent application number 10-2006-0066085 by the applicant, the contents of which are incorporated by reference into this disclosure as if fully set forth herein.

BACKGROUND OF THE INVENTION

1. Field of the Invention

The present invention relates to a novel compound isolated from *Ginkgo biloba* and a method for isolating the same, and more particularly to a novel compound isolated from the *Ginkgo biloba* bark, which is used for the treatment of thrombus, an antiplatelet agent containing the novel compound, and a method isolating the novel compound from *Ginkgo biloba*.

Thus, the novel compound discovered in the *Ginkgo biloba* bark according to the present invention can be considered as a very good compound for the treatment of thrombus.

2. Background of the Related Art

*Ginkgo biloba* is a deciduous tree belonging to the Ginkgoaceae family and contains many components found therein. As studies on flavonoids among the components have been actively conducted, the flavonoids have been found to have various physiological activities and pharmacological effects and have been frequently developed and marketed as medical drugs through clinical experiments.

*Ginkgo biloba* is known to contain large amounts of physiologically active substances.

The fruit of *Ginkgo biloba* contains phenolic compounds such as ginkgol, bilobal and ginkgolic acid, and the seed of *Ginkgo biloba* contains cyanogenetic glycosides, amino acids and the like. The leaf of *Ginkgo biloba* contains aromatic compounds, particularly phenolic compounds, flavonoid glycosides, simple flavonoids such as keampferol, quercetin, isorhamnetin and luteolin, and terpenoid compounds such as ginkgolide and bilobalid.

Studies associated with *Ginkgo biloba* have been mostly conducted to date on the leaf or fruit of *Ginkgo biloba*, but it is an object of the present invention to provide a method for isolating and purifying a novel compound from the *Ginkgo biloba* bark, which has been little studied.

According to data reported by Korea National Statistical Office in 2000, circulatory system diseases such as arteriosclerosis, cerebral hemorrhage, cerebral stroke and cerebral infarction are adult diseases, which are the first and second leading causes of death. Such adult diseases frequently occur in the middle- and old-age groups due to the change of dietary life styles, and external and internal environmental stresses, as society develops. The main cause of these diseases is known to be thrombus, which is recognized as a pathological phenomenon mediated by excessive platelet aggregation. Meanwhile, when blood vessels are damaged, platelets are activated by stimulation with various agonists such as collagen, thrombin and adenosine diphosphate (ADP) and are subjected to adhesion, secretion and aggregation. Such reactions are involved in hemostasis, but perform an important role in the onset circulatory system diseases, including thrombosis.

According to prior reports, when platelets are stimulated with collagen, thrombin, ADP and adrenaline, phospholipase C present in the platelet membrane is activated to degrade phosphatidylinositol 4,5-bisphosphate (PIP 2), thus producing diacyl glycerol (DG) and inositol-1,4,5-trisphosphate (IP). The produced DG activates protein C-kinase to induce the phosphorylation of 40 KDa protein and the activation of DG-lipase and MG(monoacyl glycerol)-lipase, thus inducing the release of arachidonic acid into the cytoplasm. The released arachidonic acid is converted into PGG 2 (prostaglandin prostaglandin G2)/PGH 2 (prostaglandin H2) by cyclooxygenage, from which tromboxane A 2 (TX A 2) is produced. The tromboxane is importantly involved in blood coagulation, platelet aggregation and thrombus formation.

Aspirin, which has been used as an antiplatelet agent for a long period of time, is a salicin derivative, an active ingredient from the willow bark, and shows high activity, even though it has low cost. However, clinical physicians increasingly guard against the use of aspirin due to the risk of bleeding caused by aspirin.

Currently, plavix is antiplatelet agent in the antiplatelet market, but causes side effects such as bleeding, diarrhea and abdominal pain.

Antiplatelet agents developed to date include theopylline, molsidomine, verapamil and nifedipine, which are known to inhibit the release of $Ca^{2+}$ by stimulating the production of cAMP and cGMP, and nonsteroidal compounds such as aspirin, imidazole and indomethacin, which are known to act as antiplatelet agents by inhibiting the production of TXA 2. However, antiplatelet preparations, including the above-mentioned drugs, anticoagulants, and thrombolytic agents, are all purified chemical substances, and have a problem in that they cause various side effects, including excessive hemostasis, sterility and digestive disorders, when administered to the human. In other words, the drugs developed to date can prevent and treat cerebral hemorrhage, cerebral thrombosis, cerebral infarction, cardiac thrombosis, arteriosclerosis and other circulatory system diseases by suppressing the formation of thrombus, which is the main cause of these diseases, and the aggregation of platelets, which mediate the formation of thrombus. However, these medical drugs have a limitation in the use thereof due to the side effects thereof. Thus, it is urgently required to develop a natural antithrombotic agent, which is harmless to the human and are free of side effects.

As described above, the antiplatelet agents developed to date involve side effects, because these are not based on natural substances. On the other hand, the present invention relates to a novel natural compound isolated from the bark of *Ginkgo biloba*. In the present invention, the antiplatelet activity of the novel compound was measured.

Although blood flow improvers such as Gingkomin, Ginexin and Circulan, based on natural substances, have been marketed, these are all preparations based on components extracted from the leaf of *Ginkgo biloba* and can be considered as mixtures of various substances, but not single compound. On the other hand, in the present invention, a single compound isolated from *Ginkgo biloba* was confirmed to have antiplatelet activity.

Recently, the use of antiplatelet agents has been greatly increased due to the rapid increase of vascular diseases. Typical examples thereof are "aspirin" and "plavix". Aspirin is an antiplatelet agent, which has been used for a very long time, and plavix is another typical antiplatelet agent, which currently leads the antiplatelet market. However, patients who received stenting to enlarge cardiovascular vessels because of angina caused by coronary arteriosclerosis (after this stenting, stent thrombosis in which thrombus is formed in the stent to block blood flow occurs) are usually administered with antiplatelet agents, aspirin and plavix. However, it was recently found that, in the case of patients in which liver enzyme CYP3A5 is not activated, aspirin and plavix have little or no effect. Thus, thrombosis therapeutic agents of various pathways should be developed for more safer treatment, and a combined therapy of antithrombotic agents having various mechanisms receives great attention, compared to a single therapy. That is, because mechanisms in which thrombus is formed are different, a need for drugs having various mechanisms exists.

SUMMARY OF THE INVENTION

The present inventors have conducted studies on the bark of *Ginkgo biloba* to solve the above-described problems occurring in the prior art and, as a result, found that a compound obtained by extracting the *Ginkgo biloba* bark with a solvent and fractionating the extract to isolate the compound was measured to show antiplatelet activity. Thus, an object of the present invention is to provide a novel compound showing antiplatelet activity.

Another object of the present invention is to provide a novel compound having antiplatelet activity, which is isolated from the bark of *Ginkgo biloba* by extracting the bark of *Ginkgo biloba* with a solvent and fractionating the extract, as well as a method for isolating the novel compound from the *Ginkgo biloba* bark.

Still another object of the present invention is to provide a novel compound, which can effectively inhibit platelet aggregation induced by collagen, has effects similar to those of gingkolide A and B as the active ingredients of a *Ginkgo biloba* leaf extract, can be isolated from the leaf and bark of *Ginkgo biloba* using isolation technology, can be used by itself as a new natural antithrombotic drug compound and can be used as a lead compound to develop new drugs by making its derivatives having structural activity relationship.

Yet another object of the present invention is to provide an antiplatelet composition, which is a new single-component natural drug substance and has reduced side effects such as hemorrhage caused by the excessive use of aspirin.

To achieve the above objects, the present invention provides 5-(3-hydroxyprophyl)-6-methoxy-2-(3'-methoxy-4'-hydroxyphenyl)-3-benzo[b]furancarbaldehyde of Formula (1), a novel compound isolated from *Ginkgo biloba*, as well as an antiplatelet agent containing said compound:

[Formula 1]

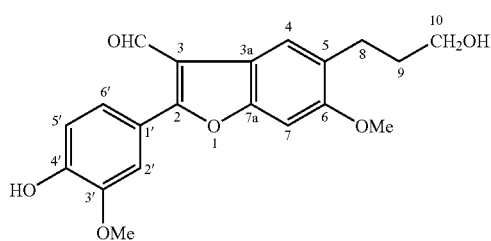

The novel compound of Formula (1) shows antiplatelet activity.

Also, the present invention provides a pharmaceutical composition for antiplatelet agents, comprising the novel compound of Formula (1). This pharmaceutical composition for antiplatelet agents can be administered orally or parenterally and be used in the form of general medical preparations. The composition comprising the novel compound of Formula (1) can be formulated into preparations, including powders, granules, tablets, capsules and injection solutions, by mixing it with a pharmaceutically acceptable carrier, excipient, diluent or like.

The antiplatelet activity of the novel compound represented by Formula (1) can be measured by the activity thereof against collagen-stimulated platelet aggregation.

The novel compound of Formula (1) according to the present invention can be used alone or in a mixture with a pharmaceutically or sitologically acceptable excipient or diluent in drugs, beverages and foods.

Also, the present invention provides a method for isolating the novel compound, which can be represented by Formula (1), from the bark of *Ginkgo biloba*.

The inventive method for isolating the novel compound, which can be represented by Formula (1), from the bark of *Ginkgo biloba*, comprises the steps of: separating *Ginkgo biloba* into bark and xylem; grinding the bark and extracting the ground material with alcohol to obtain a crude extract; fractionating the *Ginkgo biloba* bark crude extract with an organic solvent; fractionating the solvent fractions by Sephadex column chromatography; and fractionating the Sephadex fractions by silica gel column chromatography.

The *Ginkgo biloba*, which can be used to isolate the novel compound of Formula (1), may be any one from among the leaf, xylem, bark and root of the *Ginkgo biloba*, preferably a mixture of two or more thereof, and more preferably a mixture of two or more having the same ratio between the components.

The alcohol, which is used in the crude extraction of the *Ginkgo biloba* bark, may be ethanol, methanol or a mixture thereof.

The crude extract from the *Ginkgo biloba* bark can be fractionated using the organic solvent. As the organic solvent, any organic solvent can be used as long as it is a conventionally used organic solvent. Examples of the organic solvent, which can be used in the present invention, include light petroleum ether (LPE), methylene chloride ($CH_2Cl_2$), ethyl acetate (EtOAc), and mixtures thereof.

The *Ginkgo biloba* bark fractions subjected to the solvent fractionation are additionally fractioned by Sephadex column chromatography, and the Sephadex fractions are further fractionated by silica gel column chromatography. The resulting fractions can be analyzed by electron impact ionization mass spectra (EI-MS spectra) and nuclear magnetic resonance spectra (NMR spectra) in order to confirm the novel compound of Formula (1).

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION OF THE PREFERRED EMBODIMENT

Hereinafter, the present invention will be described in detail with reference to examples. It is to be understood, however, that these examples are for illustrative purposes only and are not to be construed to limit the scope of the present invention.

Example 1

Isolation of *Ginkgo biloba* Bark Fraction

A ground *Ginkgo biloba* bark was extracted with methanol to obtain a crude extract of the bark.

The crude extract was subjected to solvent fractionation to obtain a methylene chloride soluble portion (GBD).

The methylene chloride soluble portion was fractionated by Sephadex column chromatography (MeOH:EtOH=1:1) to obtain 50 ml of each of 90 fractions. Each of these fractions was developed by thin layer chromatography (TLC; silica gel 60 F$^{254}$) using a mixture of toluene:ethyl formate:formic acid=5:4:1 (v/v/v) as a developing solvent, was visualized with a UV lamp (254 nm) and separated into five fractions (GBD-1 to GBD-5).

Among said five fractions, the GBD-2 fraction was fractionated by Sephadex column chromatography (MeOH:H$_2$O=3:1), and 10.0 g of each of 100 fractions was collected by a fraction collector. These fractions were separated into six fractions (GBD-2-1 to GBD-2-6).

Among said six fractions, the GBD-2-5 fraction was fractionated by silica gel column chromatography (CHCl$_3$:MeOH=100:1) to obtain 20.0 g of each of 250 fractions. These fractions were separated into five fractions (GBD-2-5-1 to GBD-2-5-5).

Among said five fractions, the GBD-2-5-2 fraction was purified by preparative TLC (CHCl$_3$:MeOH=10:1 to CHCl$_3$:MeOH=3:1) to obtain GBD-2-5-2A.

Example 2

Figure 1:
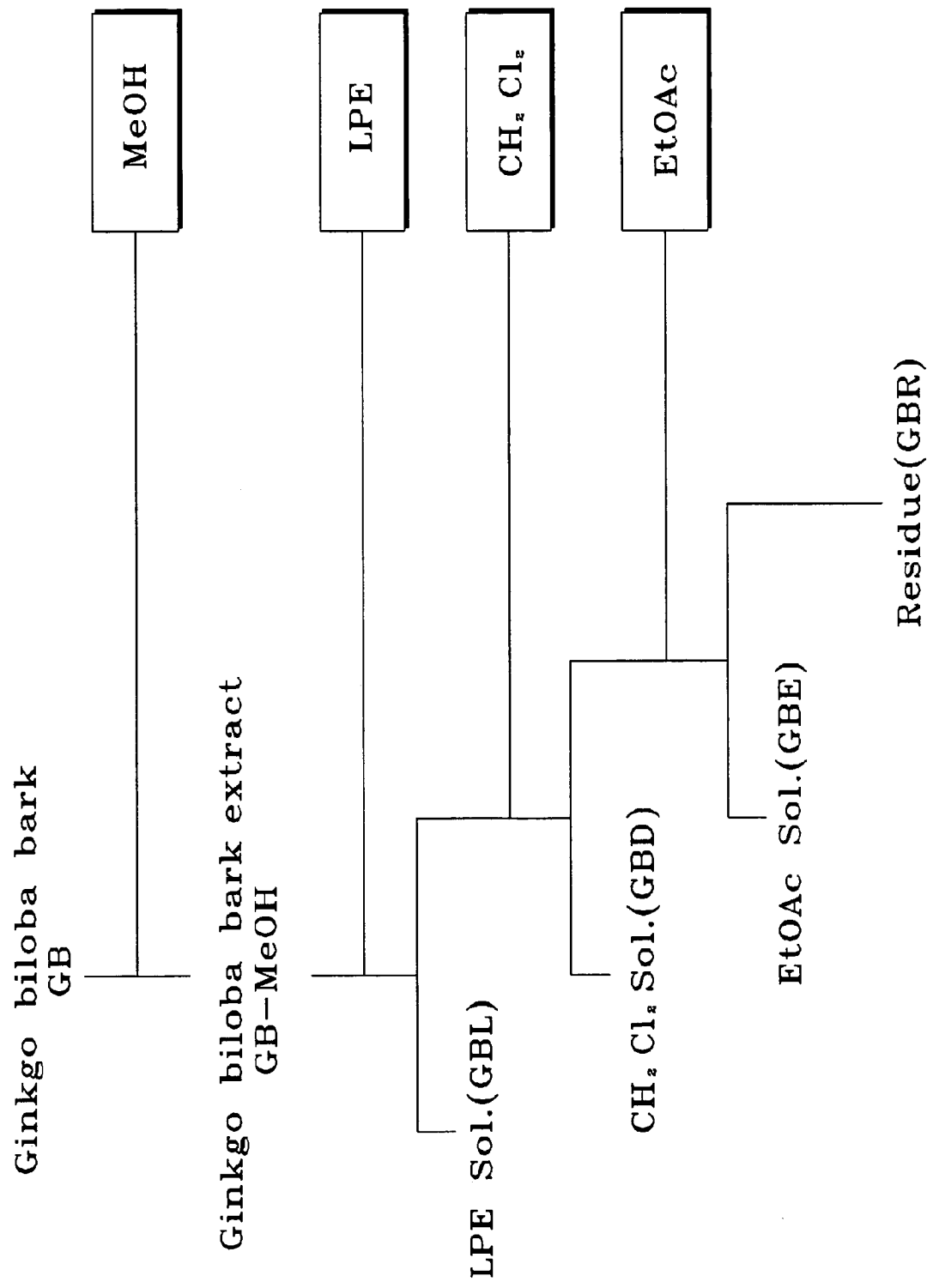
FIG. 1 is a schematic diagram showing a process for fractionating the *Ginkgo biloba* bark.
Figure 2:
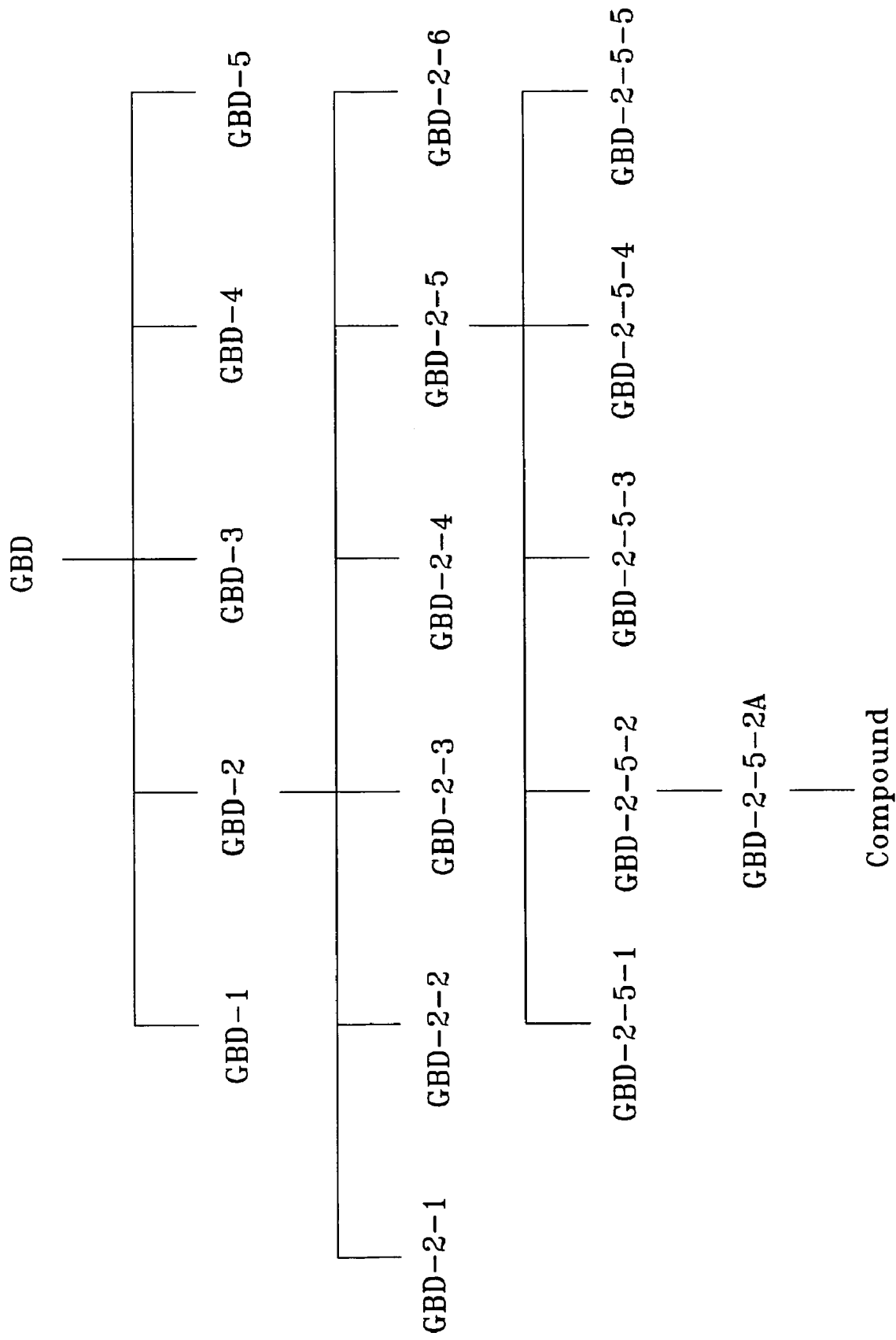
FIG. 2 is a schematic diagram showing a process of isolating a novel compound from GBD which is a *Ginkgo biloba* bark methylene chloride ($CH_2Cl_2$) fraction of FIG. 1.
Figure 3:
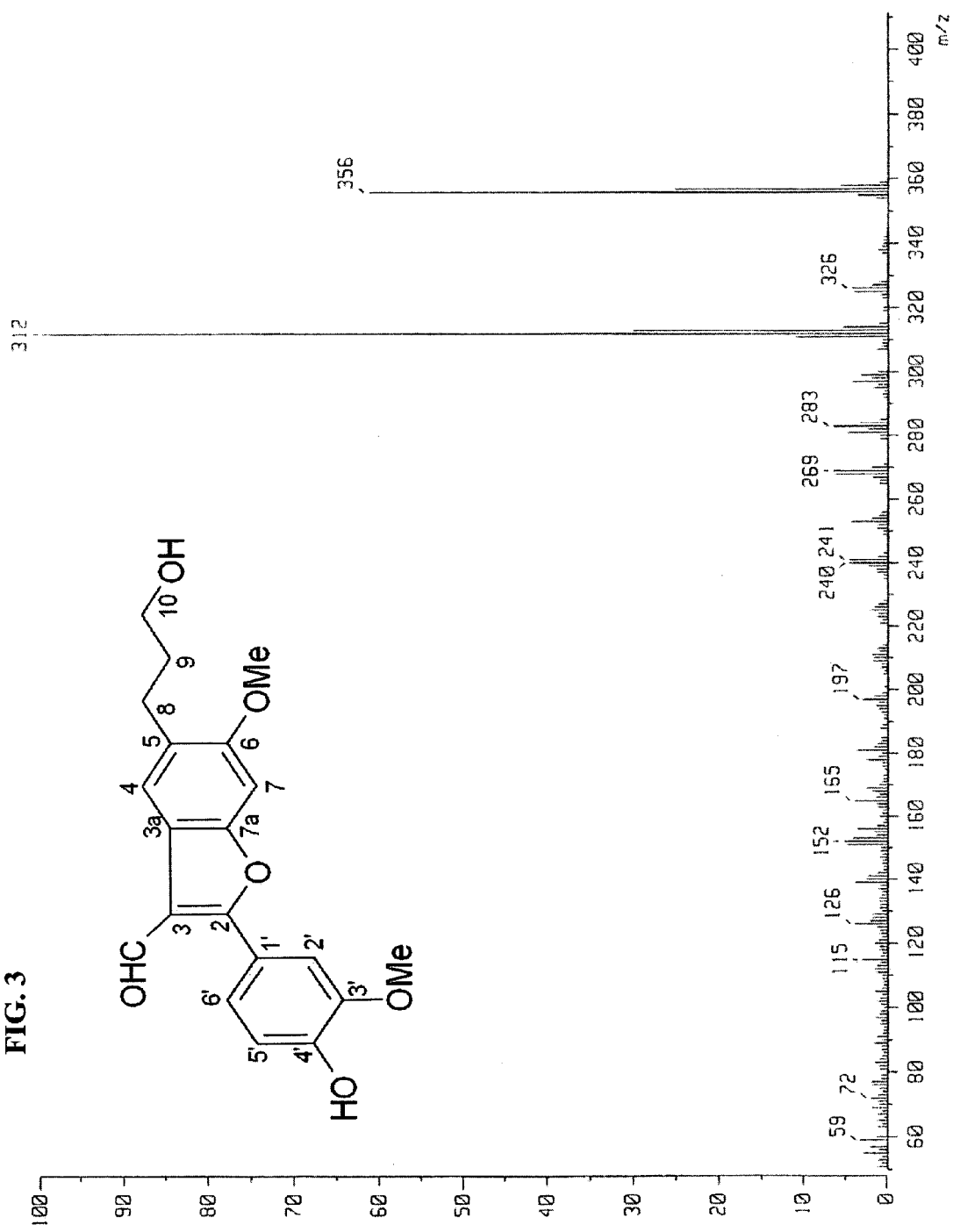
FIG. 3 is the EI-MS spectrum of GBD-2-5-2A of FIG. 2.
Figure 4:
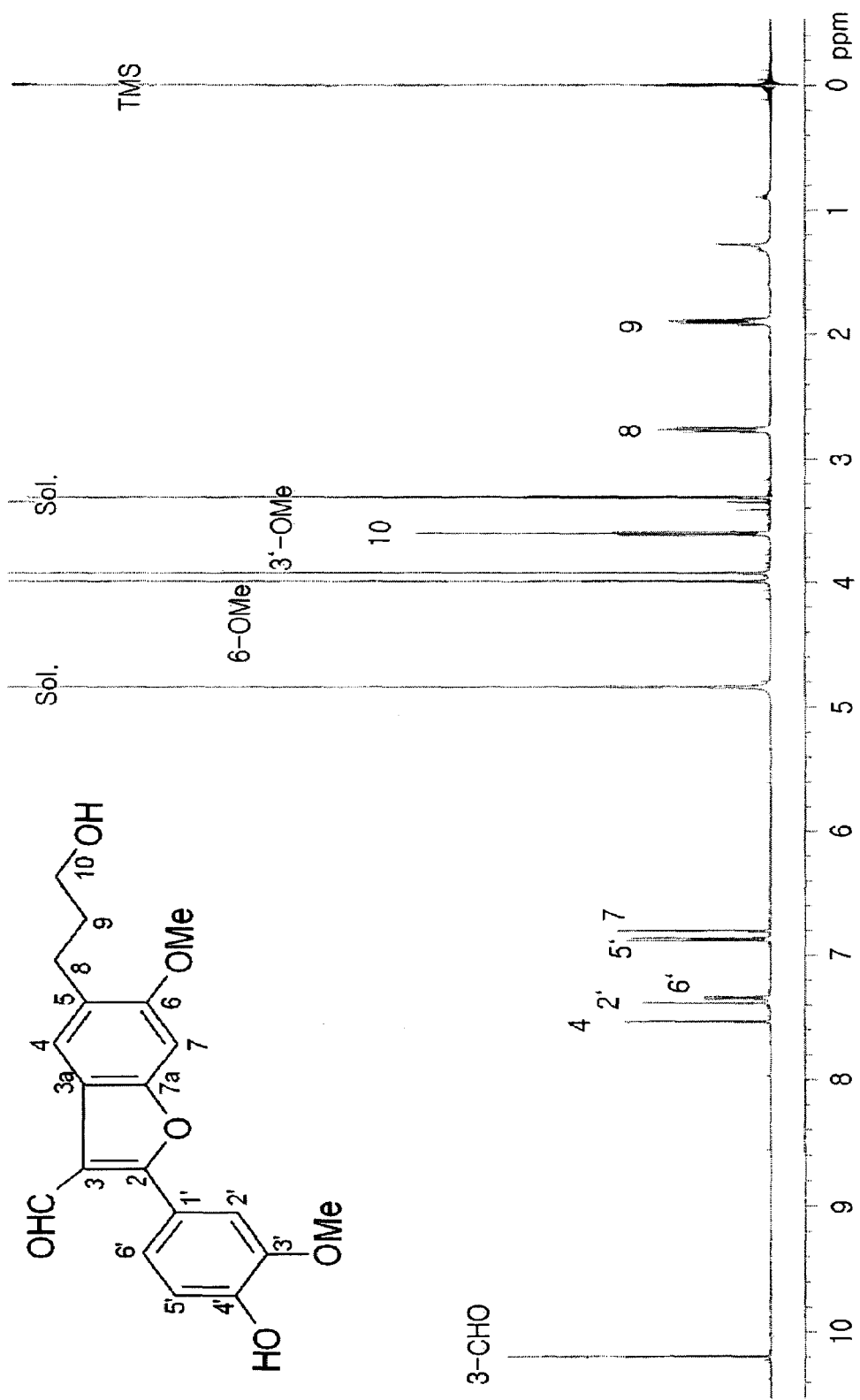
FIG. 4 is the $^1$H-NMR spectrum of GBD-2-5-2A of FIG. 2.
Figure 5:
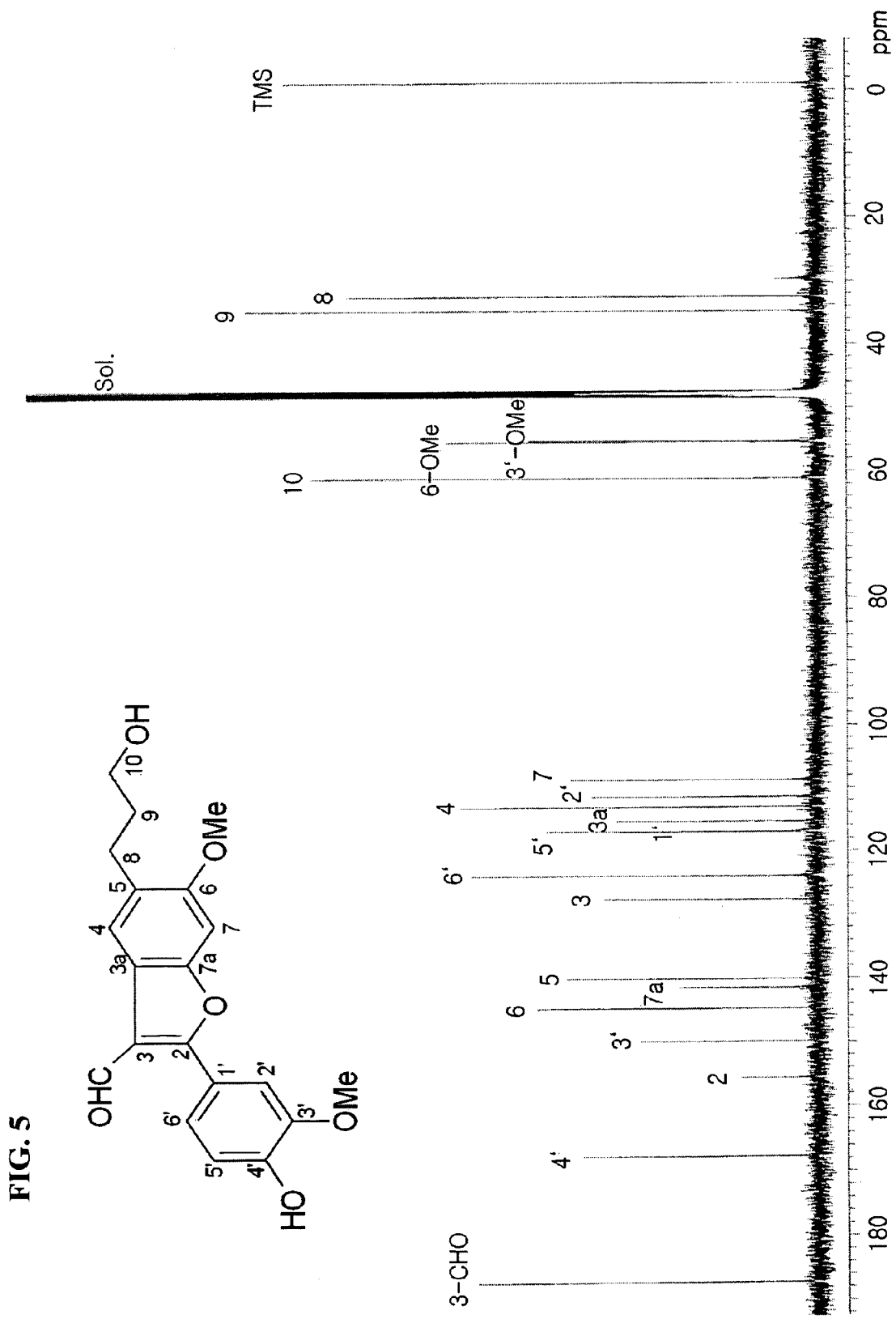
FIG. 5 is the $^{13}$C-NMR spectrum of GBD-2-5-2A of FIG. 2.

On the GBD-2-5-2A fraction obtained in Example 1, EI-MS (electron impact ionization mass spectrometer) were measured using JEOL JMS-SX102A (JEOL LTD, Japan). Also, 1D NMR (1 dimensional nuclear magnetic resonance) measurements, including $^1$H-NMR, $^{13}$C-NMR and DEPT (distortionless enhancement by polarization transfer) spectra, and 2D NMR spectra, including $^1$H-$^1$H COSY (correlation spectroscopy), NOESY (nuclear overhauser and exchange spectroscopy), TOCSY (totally correlated spectroscopy), HMQC (heteronuclear multiple quantum coherence) and HMBC (heteronuclear multiple bond coherence) spectra, were measured using Varian Unity-Inova 500 MHz. As an internal standard, TMS (tetramethylsilane) was used, and as a solvent, methanol-d$_4$ was used. The measurement results are shown in FIGS. 3, 4 and 5.

EI-MS m/z: 356 ([M]$^+$, molecular ion), 312 (base ion).

HREI-MS m/z: 356.1268 ([M]$^+$, calcd. for C$_{20}$H$_{20}$O$_6$, 356.1268).

$^1$H-NMR (500 MHz, methanol-d$_4$): δ 1.89 (2H, m, H-9), 2.76 (2H, t, J=7.5, 15.5 Hz, H-8), 3.60 (2H, t, J=7.0, 13.5 Hz, H-10), 3.92 (3H, s, 3'-OMe), 3.99 (3H, s, 6-OMe), 6.80 (1H, s, H-7), 6.86 (1H, d, J=8.5 Hz, H-5'), 7.33 (1H, dd, J=2.0, 8.5 Hz, H-6), 7.38 (1H, d, J=2.0 Hz, H-2'), 7.53 (1H, s, H-4), 10.19 (1H, s, 3-CHO).

$^{13}$C-NMR (125 MHz, methanol-d$_4$): δ 32.38 (t, C-8), 34.72 (t, C-9), 55.23 (q, 3'-OMe), 55.44 (q, 6-OMe), 61.13 (t, C-10), 108.70 (d, C-7), 111.41 (d, C-2'), 113.04 (d, C-4), 115.32 (s, C-3a), 116.88 (s, C-1'), 116.97 (d, C-5'), 123.89 (d, C-6'), 127.59 (s, C-3), 140.11 (s, C-5), 141.45 (s, C-7a), 144.77 (s, C-6), 149.89 (s, C-3'), 155.64 (s, C-2), 167.74 (s, C-4'), 187.36 (d, 3-CHO).

COSY: H-9↔H-8/H-10, H-5'↔H-6'.

NOESY: H-9↔H-8/H-10, H-8↔H-10/H-4', 3'-OMe↔H-2', 6-OMe↔H-7, H-5'↔H-6', H-6'↔3-CHO.

HMBC: H-9→C-8/C-10/C-5, H-8→C-9/C-10/C-4/C-5, H-10→C-8/C-9, 3'-OMe→C-3, 6-OMe→C-6, H-7→C-7a, H-5→C-1'/C-3', H-6→C-2'/C-2/C-4', H-2'→C-6'/C-3'/C-2/C-4', H-4→7a, 3-CHO→C-3a/C-3.

As can be seen from the measurement results, the GBD-2-5-2A fraction was 5-(3-hydroxyprophy)-6-methoxy-2-(3'-methoxy-4'-hydroxyphenyl)-3-benzo[b]furancarbaldehyde represented by Formula (1):

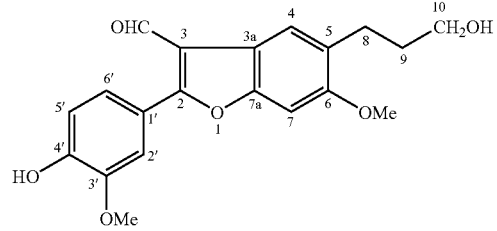

The compound of Formula (1) had a molecular formula C$_{20}$H$_{20}$O$_6$ and a molecular weight of 356.

Test Example 1

Measurement of Antiplatelet Activity

The antiplatelet activity of 5-(3-hydroxyprophyl)-6-methoxy-2-(3'-methoxy-4'-hydroxyphenyl)-3-benzo[b]furancarbaldehyde, the novel compound of Formula 1 isolated from the *Ginkgo biloba* bark in Example 1, was measured.

To measure the activity against collagen-stimulated platelet aggregation of the novel compound identified from the *Ginkgo biloba* bark, concentrated human platelet-rich-plasma (PRP) was first prepared. The PRP used in the present invention was obtained by collecting blood from volunteers in Hallym University Medical Center, centrifuging the blood at 1,000 rpm and room temperature for 10 minutes to collect pure supernatant PRP and centrifuging the supernatant PRP at 3,000 rpm and room temperature for 10 minutes. The obtained PRP was separated into platelet-poor plasma (PPP) and platelets (PLTs). Then, concentrated PRP was prepared in the following manner. That is, platelets (PLTs) were suspended in a suitable amount of the supernatant PPP and measured for absorbance at 660 nm using a UV/visible spectrophotometer. Based on the measured absorbance, the suspension was further diluted with an excess of PPP to prepare concentrated PRP containing $5 \times 10^8$ platelets/ml. Herein, an OD value of 1.1 at 660 nm means $1 \times 10^8$ PLTs. A washing buffer used in the present invention was a pH 6.5 buffer containing 129 mM NaCl, 10.9 mM sodium citrate dihydrate, 8.9 mM $NaHCO_3$, 1 mg/ml glucose, 10 mM tris-hydroxymethylaminomethane, 2.8 mM KCl, 0.8 mM $KH_2PO_4$ and 2 mM EDTA. Also, a suspension buffer used in this test example was a pH 6.9 buffer, which was the same as said washing buffer, except that it contained no EDTA.

The platelet aggregation inhibitory effect of the novel compound was examined using the prepared concentrated PRP in the following manner. First, the concentrated PRP was used to make 500 μl of an in vitro reaction system. For use as a control group, the concentrated PRP was stabilized at 37° C. for 3 minutes and treated with collagen (Chrono-LogCo.) as a stimulating agent at a concentration of 10 μg/ml, and the aggregation of platelets in the reaction system was induced for 5 minutes. Meanwhile, the same reaction system as described above was treated with the novel compound, was allowed to react with the novel compound for 3 minutes, was stimulated with collagen for 6 minutes according to the same method as described above so as to induce platelet aggregation, and then was measured for aggregated platelets. The aggregation of platelets was measured with a change in light transmission using an aggregometer (Chrono-Log Co.) at 37° C. The measurement results are shown in Table 1 below and FIGS. 6, 7 and 8.

Table 1 summarizes the antiplatelet aggregation activities of aspirin, the novel compound and ginkgolide A and B against platelet aggregation factors, including ADP, collagen and arachidonic acid. As shown in Table 1, aspirin showed $IC_{50}$ (half maximal inhibitory concentration) values of 316 μM and 203 μM against aggregation factors ADP and collagen, respectively, and the novel compound and ginkgolide A and B did not show an effect against the aggregation factor ADP, but showed $IC_{50}$ values of 680, 482 and 480 μM, respectively, against collagen-stimulated platelet aggregation. In the case of the group treated with the novel compound, when arachidonic acid was used as the aggregation factor, the aggregation of platelets occurred only upon stimulation with 1,000 μM (i.e., 1 mM) or higher concentration of arachidonic acid. In the case of the groups treated with ginkgolide A and B, arachidonic acid-stimulated platelet aggregation did not occur.

Figure 6:
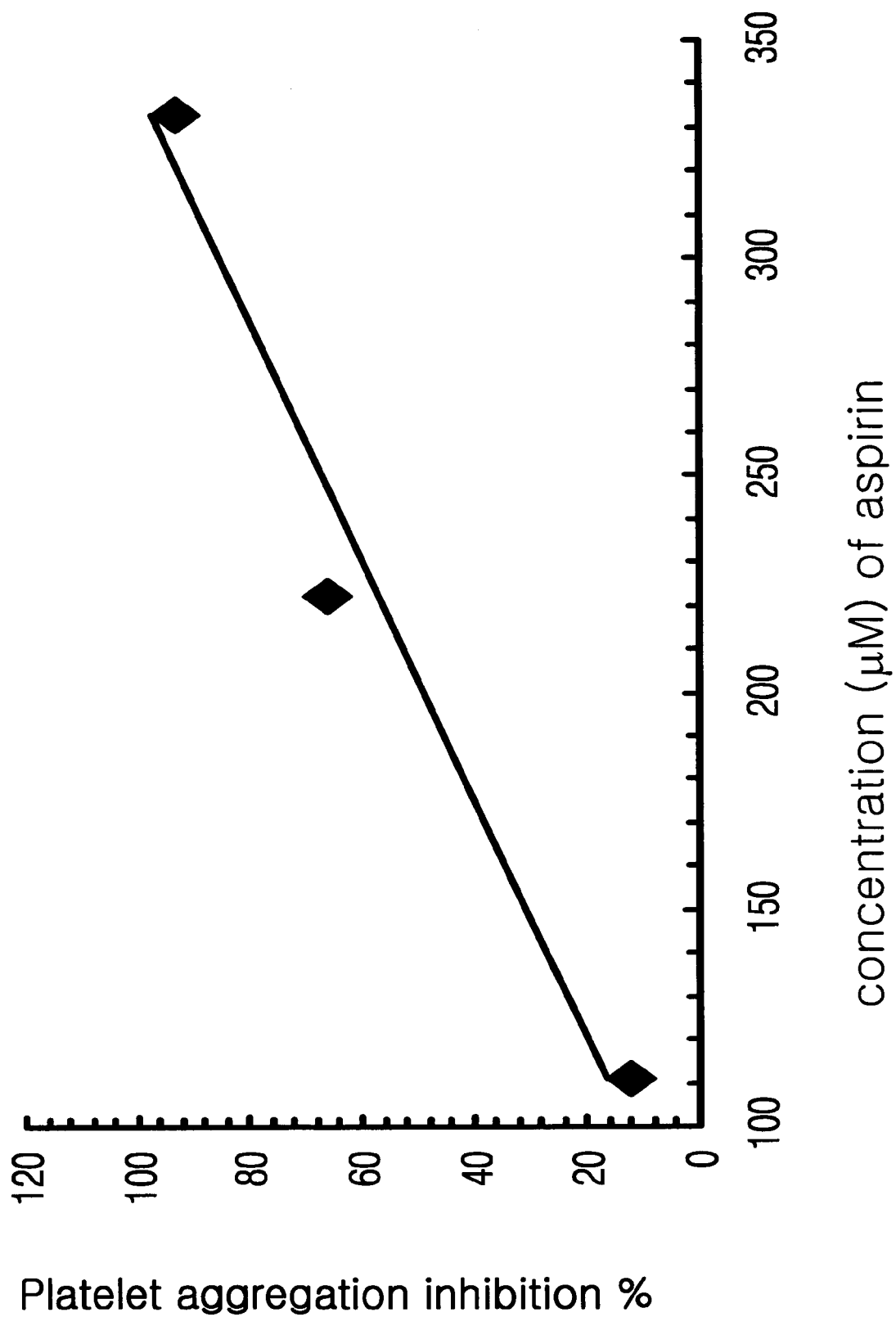
FIG. 6 is a graphic diagram showing the platelet antiaggregation activity of aspirin against collagen-induced platelet aggregation.
Figure 7:
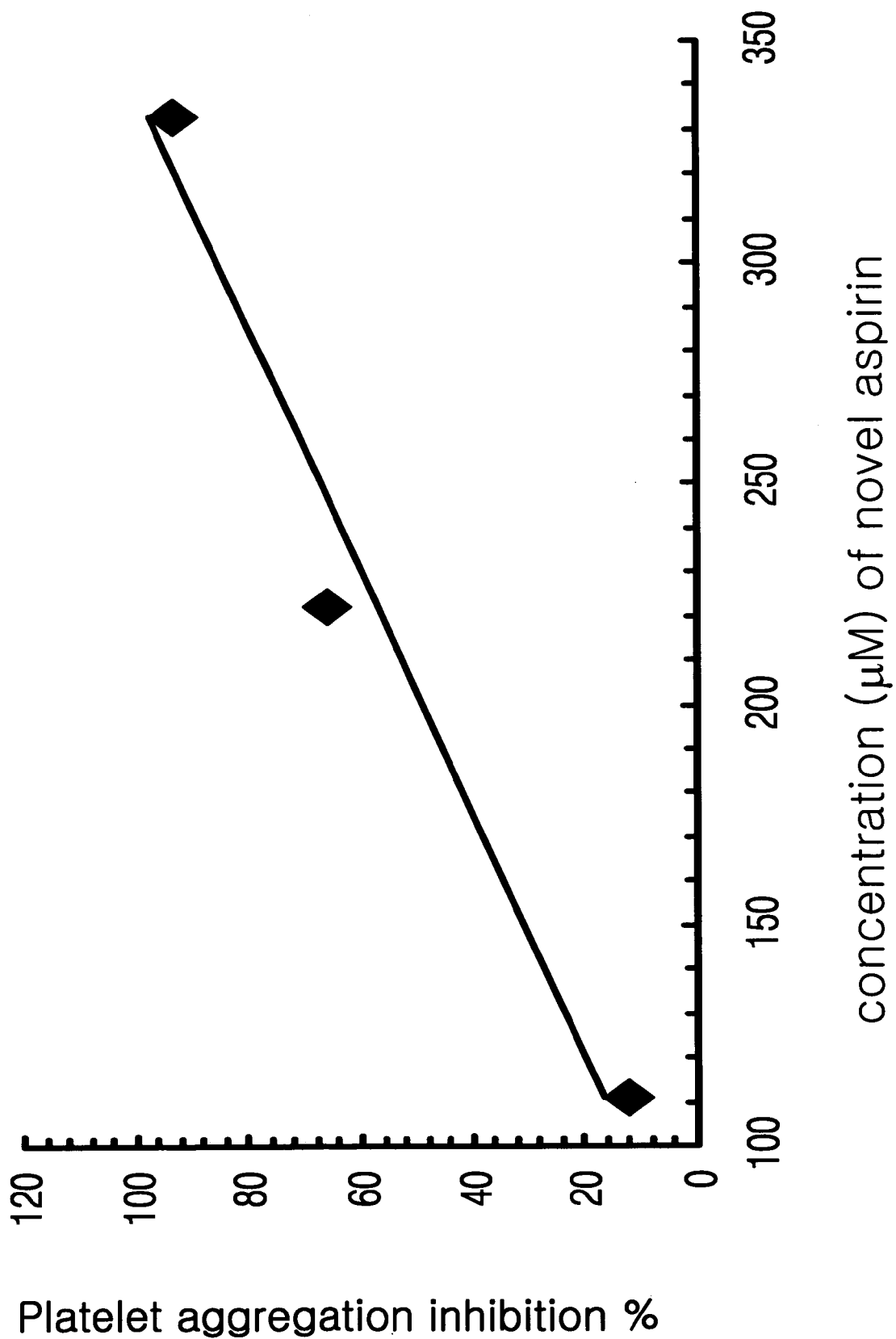
FIG. 7 is a graphic diagram showing the platelet antiaggregation activity of GBD-2-5-2A of FIG. 2 against collagen-induced platelet aggregation.
Figure 8:
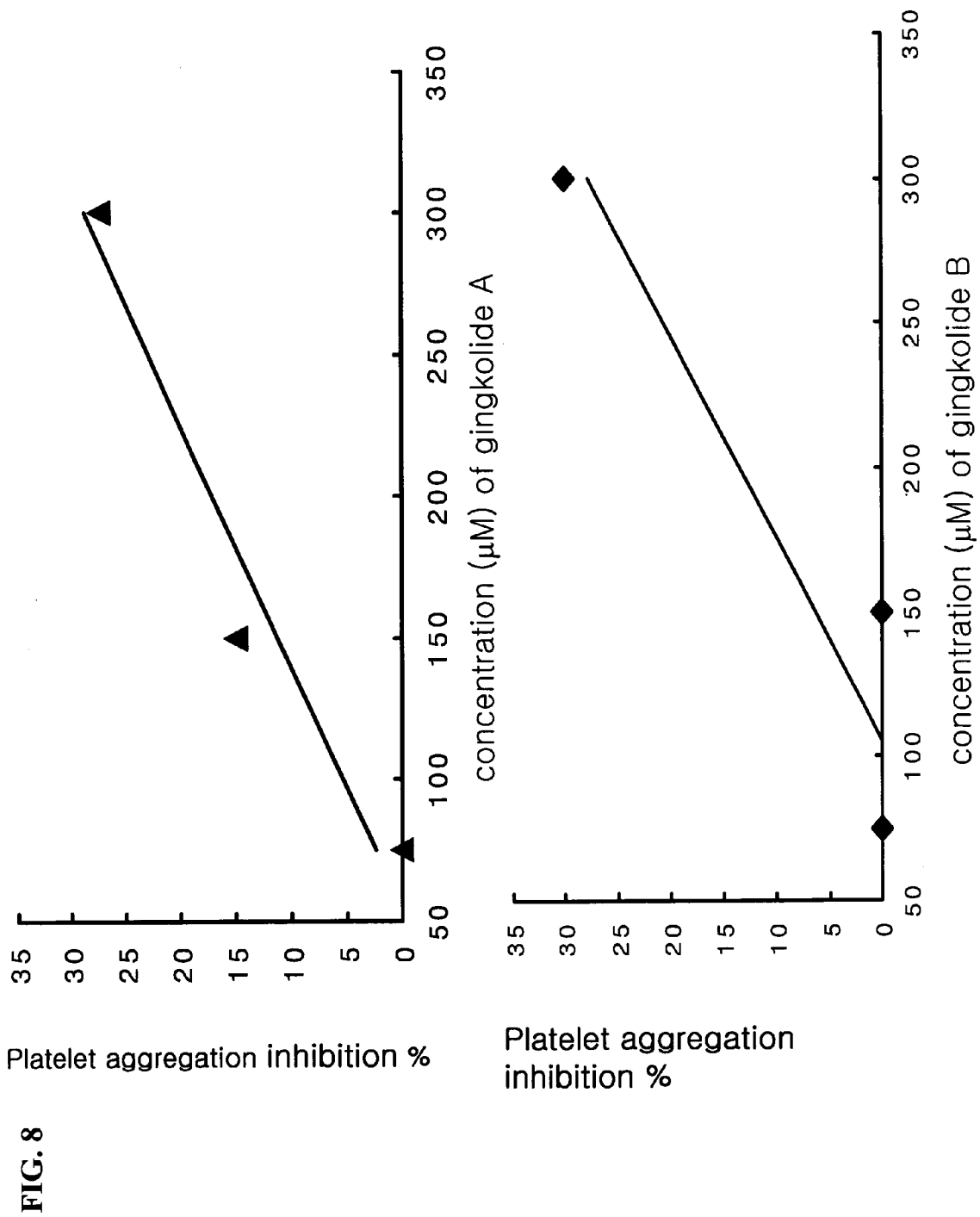
FIG. 8 is a graphic diagram showing the platelet antiaggregation activities of gingkolide A and B against collagen-induced platelet aggregation.

FIG. 6 is a graphic diagram showing the inhibitory activity of aspirin on collagen-stimulated platelet aggregation. As shown in FIG. 6, aspirin inhibited platelet aggregation in a concentration-dependent manner. FIG. 7 is a graphic diagram showing the inhibitory activity of the novel compound isolated from Ginkgo biloba on collagen-stimulated platelet aggregation. As shown in FIG. 7, the novel compound inhibited collagen-stimulated platelet aggregation in a concentration-dependent manner. FIG. 8 is a graphic diagram showing the inhibitory effect of each of gingkolide A and B on collagen-stimulated platelet aggregation. As shown in FIG. 8, each of gingkolide A and B inhibited collagen-stimulated platelet aggregation in a concentration-dependent manner.

TABLE 1

Antiplatelet aggregation activities of aspirin, novel compound and gingkolide A and B

| | $IC_{50}$ (μM) | | |
|---|---|---|---|
| Compounds | ADP | Collagen | AA |
| Aspirin | 316 | 203 | N.D |
| Novel compound | — | 680 | >1,000 |
| Gingkolide A | — | 482 | — |
| Gingkolide B | — | 480 | — |

N.D = not determined
—: no effect

As described above, it can be seen from said Example and Test Example that the inventive novel compound isolated from the Ginkgo biloba bark has antiplatelet activity. Thus, according to the present invention, the novel compound isolated from the Ginkgo biloba bark can be provided.

Also, the novel compound according to the present invention is a natural substance, and thus has no side effects caused by synthetic compounds. Also, the novel natural compound having antiplatelet aggregation activity can be extracted from the leaf or bark of Ginkgo biloba and used as a natural antithrombotic agent having collagen-stimulated platelet aggregation effects.

Moreover, the novel compound isolated from the Ginkgo biloba bark can inhibit thrombus formation induced by collagen.

Furthermore, the novel compound can may inhibit serotonin secretion caused by collagen, which performs an important role in thrombus formation. Also, it can may inhibit the activity of guanylate cyclase acting as a mediator in a mediator in a signaling process associated with thrombus formation and inhibit an increase in intracellular calcium ions as secondary signaling substances of thrombus formation.

In addition, the inventive novel compound shows effects similar to those of gingkolide A and B, which have been used as antithrombotic compounds in the prior art. Thus, a composition containing the novel compound has excellent antithrombotic effects and can be used for the treatment of diseases, including arteriosclerosis, cerebral hemorrhage, cerebral stroke and cerebral infarction, which involve thrombosis.

Although the preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:
1. A compound isolated from the bark of Ginkgo biloba and represented by the following formula:

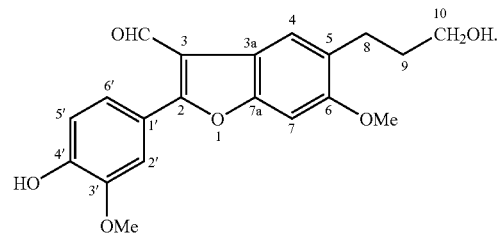

2. A method for isolating a compound represented by the following formula, the method comprising the steps of:
   (1) extracting *Ginkgo biloba* with alcohol to obtain a crude extract;
   (2) subjecting the *Ginkgo biloba* crude extract to solvent fractionation using an organic solvent;
   (3) fractionating the solvent fractions by Sephadex column chromatography; and
   (4) fractionating the Sephadex fractions by silica gel column chromatography:

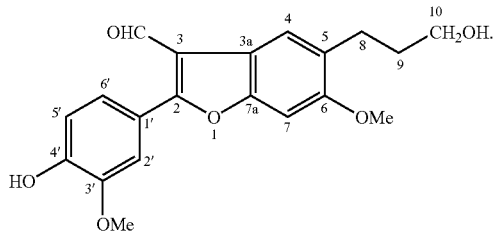

3. The method of claim 2, wherein the *Ginkgo biloba* used in said step (1) is any one selected from the bark, xylem, root and leaf of *Ginkgo biloba*, or a mixture of two or more thereof.

4. The method of claim 2, wherein the alcohol used in said step (1) is methanol, ethanol, or a mixture thereof.

5. The method of claim 2, wherein the organic solvent is selected from the group consisting of light petroleum ether (LPE), methylene chloride ($CH_2Cl_2$), ethyl acetate (EtOAc), and mixtures thereof.

6. An antiplatelet composition containing a compound of the following formula, said compound being isolated from the bark of *Ginkgo biloba* and acting as an inhibitor against collagen-stimulated platelet aggregation:

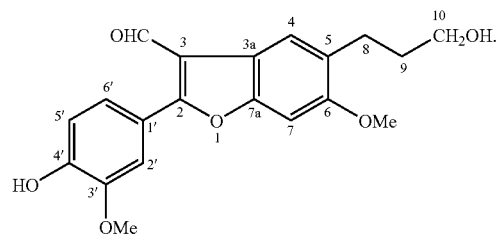

7. The composition of claim 6, which is in the form of a pharmaceutical preparation, which can be administered orally or parenterally.

8. The composition of claim 6, wherein the pharmaceutical preparation is prepared in the form of a powder, a granule, a tablet, a capsule or an injection solution by mixing the compound with a pharmaceutically acceptable carrier, excipient or diluent.

\* \* \* \* \*